United States Patent [19]

Rossi et al.

[11] Patent Number: 5,149,796
[45] Date of Patent: Sep. 22, 1992

[54] CHIMERIC DNA-RNA CATALYTIC SEQUENCES

[75] Inventors: John J. Rossi, Glendora; Pairoj Chang, Colton; Bruce E. Kaplan, Claremont, all of Calif.

[73] Assignee: City of Hope, Duarte, Calif.

[21] Appl. No.: 675,921

[22] Filed: Apr. 30, 1991

Related U.S. Application Data

[63] Continuation-in-part of Ser. No. 401,613, Aug. 31, 1989.

[30] Foreign Application Priority Data

Jun. 5, 1990 [WO] World Int. Prop. O. .......... PCT/US90/03102

[51] Int. Cl.$^5$ .......... C07H 17/80
[52] U.S. Cl. .......... 536/27
[58] Field of Search .......... 536/27

[56] References Cited

PUBLICATIONS

J. Perreault, et al. Nature, 344:565–567, 1990.
J. Haseloff, et al., Simple RNA Enzymes with New and Highly Specific Endorib. Activity Nature 334:585–591, 1988.

Primary Examiner—John W. Rollins
Attorney, Agent, or Firm—Edward S. Irons

[57] ABSTRACT

This invention provides chimeric DNA/RNA catalytic molecules useful to cleave RNA sequences.

3 Claims, 2 Drawing Sheets

FIG. 1 DRDRD-1
5'   GGUGCGAGAGCGUCAGUAUUAAGCGG   3' - HIV 792-817
3'   CCACGCTCTCGCA TCATAATTCGCC   5'
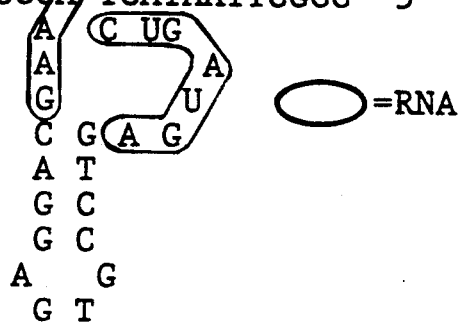
◯ = RNA
FIG. 2 DRDRD #2
5' CGACUGGUGAGUACGCCAAAA 3' - HIV LTR 737-757
3' GCTGACCTCTCA GCGGTTTT 5'
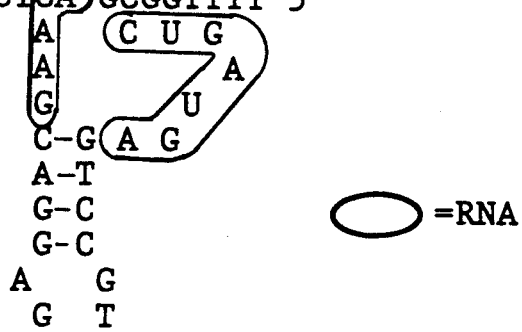
◯ = RNA

CHIMERIC DNA-RNA CATALYTIC SEQUENCES

This application is a continuation in part of application Ser. No. 401,613 filed Aug. 31, 1989.

FIELD OF THE INVENTION

This invention pertains to DNA-RNA catalytic molecules. More particularly the invention pertains to chimeric DNA-RNA-DNA-RNA-DNA catalytic molecules effective to cleave HIV-1 RNA sequences, for example.

BACKGROUND OF THE INVENTION

Ribozymes are structural RNA molecules which mediate a number of RNA self-cleavage reactions. Two distinct trans-acting ribozymes, "hammerhead" and "hairpin," having different secondary structures have been identified. Oncogenes and Aids (1990) [citation] states:

"Another possible synthetic approach is the development of a chimeric molecule containing a ribonucleotide catalytic center and deoxyribonucleotide flanking sequences. It is also conceivable that chimeric catalysts comprised of an RNA catalytic center and DNA flanking sequences will retain biological activity while having greater stability."

Perreault, et al., Nature, 344:565–567 (1990), describes certain mixed deoxyribo and ribooligonucleotides with catalytic activity. No RNA-DNA catalytic molecules of practical therapeutic utility are known.

SUMMARY OF THE INVENTION

This invention provides chimeric DNA/RNA catalytic molecules useful to cleave RNA sequences. The invention specifically provides two different chimeric DNA-RNA-DNA-RNA-DNA catalytic molecules which are targeted to cleave HIV-1 RNA sequences. These chimeric molecules include DNA sequences which flank a catalytic RNA center. Interaction with the HIV-1 substrate RNAs is achieved by Watson-Crick base pairing of the DNA flanking sequences with HIV-1 RNA. The catalytic ribonucleotide center cleaves the phosphodiester bond of the substrate HIV-1 RNA at the expected location.

GENERAL DESCRIPTION OF THE INVENTION

In general the catalytic molecules of the invention function as hammerhead or hairpin ribozymes. The preferred molecular construct consists of two known RNA catalytic sequences each flanked by a DNA sequence at the respective 3' and 5' termini and coupled by a DNA sequence at the corresponding 5' and 3' termini These molecules may accordingly be represented by the formulae I and II::

I. 3' X - AAAG - Y - AGUAGUC - Z 5' or

II. 3' X - CAAAG - Y - AGUAGUC - Z 5' in which X, Y and Z are DNA sequences and AAAG, CAAAG and AGUAGUC are catalytic RNA sequences.

The flanking X and Z components may be any DNA sequences that allow base pairing with the substrate RNA at appropriate positions adjacent to the substrate cleavage site. These flanking sequences may be phosphodiester, phosphorothioate, methyl phosphonate, methyl phosphate or similar moieties.

Y may be any DNA sequence that base pairs inter se in the manner required for catalytic cleavage of the substrate by the RNA sequences preferably as shown in base paired form in Formula III:

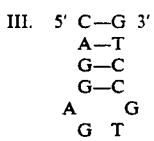

III. 5' C—G 3'
    A—T
    G—C
    G—C
   A    G
    G T

The catalytic molecules of this invention can be synthesized in known manner by commercially available DNA synthesizers such as those produced by Applied Biosystems or Milligen. See, e.g., Perreault, et al, supra.

The X and Z sequences may be substituted at the respective 3' and 5' ends with ligands to facilitate cell entry, targeting within the cell and ultimate stability of the catalysts. Such ligands include by way of example but not of limitation: other nuclotides, proteins, carbohydrates, lipids, steroid hormones and cholesterol.

The catalytic molecules of the invention are administered by known and available delivery agents or systems, including, but not limited to, liposomes, defective viral particles, viral capids, and standard DNA/RNA transfective procedures.

DESCRIPTION OF THE FIGURES

FIG. 1 illustrates one catalytic molecule of the invention base paired to an HIV-1 sequence. The RNA portion of the molecule is encircled.

FIG. 2 illustrates a second catalytic molecule of the invention base paired to another HIV-1 sequence. The RNA portion of the molecule is encircled.

EXAMPLE I

The catalytic molecule of FIG. 1 was synthesized in known manner utilizing an automated oligonucleotide synthesizer manufactured by Applied Biosystems, Inc.

Figure 3A:
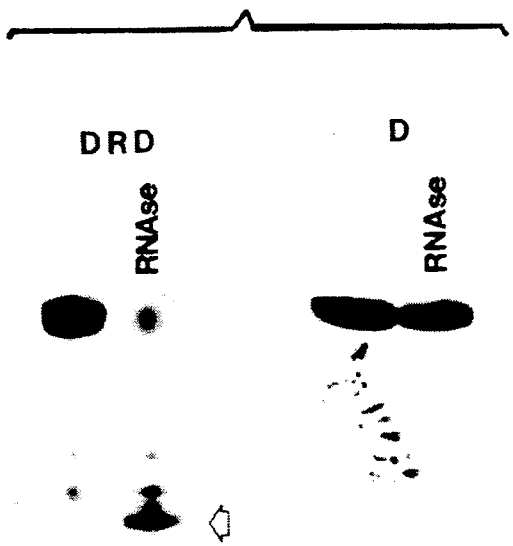
FIG. 3A depicts a ribonuclease A digestion of the catalytic molecule of FIG. 1 as compared with an equivalent all DNA molecule. The conditions were 10 units of commercial (Sigma) pancreatic ribonuclease in 2XSSC buffer added to the oligonucleotides which were in 10 microliters of 50 mM Tric-HCl buffer (pH 8.0). The RNAse was incubated with the sample for 10 minutes before the 32-P end labelled DRDRD or DNA molecules were electrophoresed in a 15% polyacrylamide gel containing 8M urea. The gel was autoradiographed for 10 minutes to get the exposure depicted.

The result of ribonuclease A digestion of the catalytic molecule is shown by FIG. 3A.

The catalytic molecule produced, as described, was used to cleave each of a 610 nuleotide long (S-610) and a 170 nucleotide long HIV-1 gag transcript. In brief, the buffer was 50 mM Tris-HCl, pH 7.5, 1mM EDTA, 10mM $MgCl_2$ at approximately 1 pmole of target, 3 pmole of ribozyme or DNA. The reactions were carried out at 37° C. for 12 hours. The substrate was either a 610 nucleotide long HIV-1 gag containing transcript (S-610) or a 172 nucleotide long HIV-1 gag containing transcript (S-172). The 5' cleavage product is indicated for both.

Figure 3B:
FIG. 3B depicts a cleavage reaction involving the catalytic molecule of FIG. 1 under conditions described in Chang, et al., Clinical Biotechnology, 2:23–31 (1990).

In FIG. 3B the 5' cleavage product is shown for both transcripts. The 3' cleavage product for the 610 target is not visible due to poor reproduction of the autoradiograph, but is indicated in its position by a 3' P notation. As a negative control, an all DNA oligonucleotide (D) of the same sequence as the DRDRD molecule was incubated with the same substrates under the same conditions with the result that no cleavage was obtained. Specific cleavage of an HIV-1 5' LTR splice site with a similar catalytic molecule has also been obtained.

We claim:

1. A catalytic molecule capable of cleaving an RNA sequence at a known ribozyme cleavage site said molecule having the formula

3' X - AAAG - Y - AGUAAGUC - Z 5' or

3' X - CAAAG - Y - AGUAAGUC - Z 5' in which X and Z are DNA sequences that base pair with an RNA substrate at positions juxtaposed to said known cleavage site, AAAG, CAAAG and AGUAGUC are RNA sequences, Y is a DNA sequence that base pairs inter se in a manner required to permit said RNA sequences to cleave said substrate at said cleavage site.

2. A catalytic molecule capable of cleaving an RNA sequence, said molecule having catalytic RNA moieties linked to first and second DNA moieties which base pair with the substrate RNA sequences flanking the cleavage site and interconnected by a third DNA sequence which base pairs inter se to facilitate said cleavage.

3. A molecule including the construct shown by FIG. 1 or FIG. 2.

* * * * *

UNITED STATES PATENT AND TRADEMARK OFFICE
CERTIFICATE OF CORRECTION

PATENT NO. : 5,149,796
DATED : September 22, 1992
INVENTOR(S) : John J. Rossi, et al.

It is certified that error appears in the above-identified patent and that said Letters Patent is hereby corrected as shown below:

Column 1, line 4, before "FIELD OF THE INVENTION", insert:

--This invention was made with government support under Grant Nos. AI 25959 and AI 39239 awarded by the National Institutes of Health. The government has certain rights in this invention.--

Claim 1, column 3, line 18, delete "AGUAAGUC" and insert --AGUAGUC--.

Claim 1, column 4, line 1, delete "AGUAAGUC" and insert --AGUAGUC--.

Signed and Sealed this

Seventh Day of March, 1995

*Attest:*

BRUCE LEHMAN

*Attesting Officer*   *Commissioner of Patents and Trademarks*